(12) United States Patent
Conklin et al.

(10) Patent No.: US 9,211,390 B2
(45) Date of Patent: Dec. 15, 2015

(54) MULTI-FUNCTIONAL WIRE GUIDE ASSEMBLY AND METHOD OF USING SAME

(71) Applicants: Hannah Conklin, Bloomington, IN (US); James Elsesser, Bloomington, IN (US); Nathan William Hecht, Bloomington, IN (US); Richard Alley, Bloomington, IN (US)

(72) Inventors: Hannah Conklin, Bloomington, IN (US); James Elsesser, Bloomington, IN (US); Nathan William Hecht, Bloomington, IN (US); Richard Alley, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 79 days.

(21) Appl. No.: 13/679,063

(22) Filed: Nov. 16, 2012

(65) Prior Publication Data

US 2013/0138052 A1    May 30, 2013

Related U.S. Application Data

(60) Provisional application No. 61/565,146, filed on Nov. 30, 2011.

(51) Int. Cl.
*A61M 25/09* (2006.01)
*A61L 29/14* (2006.01)
*A61L 31/02* (2006.01)
*A61L 31/14* (2006.01)
*A61M 25/01* (2006.01)

(52) U.S. Cl.
CPC .......... *A61M 25/09033* (2013.01); *A61L 29/14* (2013.01); *A61L 31/022* (2013.01); *A61L 31/14* (2013.01); *A61M 25/0102* (2013.01); *A61L 2400/16* (2013.01); *A61M 2025/091* (2013.01); *A61M 2025/0915* (2013.01)

(58) Field of Classification Search
CPC ............... A61M 2025/0161; A61M 25/0144; A61M 25/0152; A61M 2025/0098; A61M 2025/09175; A61M 25/0105; A61M 25/09025; A61M 25/09033; A61M 25/0053; A61M 25/0012; A61M 25/005; A61M 2025/0006; A61M 2025/09125; A61M 25/0662; A61M 25/09
USPC .............. 604/164.13, 265, 528; 600/585, 434
See application file for complete search history.

(56) References Cited

U.S. PATENT DOCUMENTS

| 4,548,206 | A | 10/1985 | Osborne |
| 4,676,249 | A | 6/1987 | Arenas et al. |
| 4,779,628 | A | 10/1988 | Machek |
| 4,895,168 | A | 1/1990 | Machek |
| 4,917,102 | A * | 4/1990 | Miller et al. .......... 600/585 |

(Continued)

*Primary Examiner* — Kami A Bosworth
*Assistant Examiner* — Brandy S Lee
(74) *Attorney, Agent, or Firm* — Liell & McNeil

(57) ABSTRACT

A multi-functional wire guide assembly includes an elongate tubular housing having a length and defining a lumen extending from an open proximal end of the elongate tubular housing to an open distal end of the elongate tubular housing. A first mandril is positioned within the lumen, extends a majority of the length of the elongate tubular housing, and has a fixed position relative to the elongate tubular housing. A second mandril is positioned within the lumen, has a length greater than the length of the elongate tubular housing, and is axially movable relative to the elongate tubular housing. The multi-functional wire guide assembly has a first configuration in which a distal tip of the second mandril is proximally spaced from a distal segment of the elongate tubular housing and a second configuration in which the distal tip of the second mandril is axially aligned with the distal segment.

15 Claims, 2 Drawing Sheets

(56) References Cited

U.S. PATENT DOCUMENTS

| | | | |
|---|---|---|---|
| 5,040,543 A * | 8/1991 | Badera et al. | 600/585 |
| 5,957,903 A | 9/1999 | Mirzaee et al. | |
| 6,270,465 B1 * | 8/2001 | Keith et al. | 600/585 |
| 2001/0009981 A1 | 7/2001 | DuBois et al. | |
| 2002/0010481 A1 * | 1/2002 | Jayaraman | 606/151 |
| 2007/0123804 A1 * | 5/2007 | Ayala et al. | 600/585 |
| 2009/0076416 A1 | 3/2009 | Treacy et al. | |
| 2009/0198153 A1 * | 8/2009 | Shriver | 600/585 |

\* cited by examiner

MULTI-FUNCTIONAL WIRE GUIDE ASSEMBLY AND METHOD OF USING SAME

RELATION TO OTHER PATENT APPLICATION

This application claims priority to provisional patent application 61/565,146, filed Nov. 30, 2011, with the same title.

TECHNICAL FIELD

The present disclosure relates generally to a multi-functional wire guide assembly, and more particularly to a wire guide assembly including a first mandril having a stationary position within a tubular housing and a second mandril that is axially movable within the tubular housing.

BACKGROUND

Diagnosis and treatment of vascular conditions are commonly performed using percutaneous vascular procedures, which may involve the insertion of a catheter or the like into a blood vessel, artery, or other passageway of the vascular system. For example, known catheterization procedures include the positioning and use of stents and balloons within constricted vessels or arteries, and the intravenous administration of bloods, drugs, and other fluids. The first step in the performance of these procedures is the establishment of a site through the skin by which access is made to the blood vessel or artery. A wire guide is then introduced into the vessel or artery and advanced to a desired location, often with the assistance of a guide catheter. A working catheter may then be advanced to the desired location over the wire guide in a safe and atraumatic fashion.

Conventional wire guides must exhibit flexibility in order to successfully navigate the tortuous passages of the vascular system, but also must have a certain amount of stiffness to pass through lesions and support other medical devices that are subsequently introduced over the wire guide. Thus, conventional wire guides, regardless of the particular application, are typically subject to conflicting requirements. Further, depending on the particular application, certain portions of the passageway being navigated may require a wire guide that is stiffer than some standard conventional wire guides, whereas other portions of the passageway may require a wire guide that is substantially more flexible than standard wire guides. As a result, a clinician may need to introduce multiple wire guides having different properties during a single procedure.

For example, during an exemplary percutaneous vascular procedure, the clinician may begin with a relatively stiff wire guide to gain access through the passageway. As the passageway becomes smaller and more tortuous, the clinician may need to replace the stiffer wire guide with a more flexible wire guide. This may be accomplished by passing a catheter over the first wire guide until the distal end of the catheter reaches the distal end of the wire guide. The first wire guide is then withdrawn from the catheter and the second wire guide is introduced through the catheter. The second, more flexible wire guide may then be advanced beyond the distal end of the catheter and through the more tortuous section of the vessel. If a lesion, or occlusion, is encountered that is difficult to pass using the second wire guide, the catheter may be advanced to increase the stiffness at the distal tip of the second wire guide. Alternatively, however, it may be desirable to replace the second wire guide with a third, relatively stiff wire guide. This need to exchange wire guides during the procedure adds to the complexity, duration, and cost of the procedure. In addition, exchanging one wire guide for another may increase the risk of contamination, and potential infection, to the patient.

The present disclosure is directed toward one or more of the problems set forth above.

SUMMARY OF THE DISCLOSURE

In one aspect, a multi-functional wire guide assembly includes an elongate tubular housing having a length and defining a lumen extending from an open proximal end of the elongate tubular housing to an open distal end of the elongate tubular housing. A first mandril is positioned within the lumen, extends a majority of the length of the elongate tubular housing, and has a fixed position relative to the elongate tubular housing. A second mandril is positioned within the lumen, has a length greater than the length of the elongate tubular housing, and is axially movable relative to the elongate tubular housing. The multi-functional wire guide assembly has a first configuration in which a distal tip of the second mandril is proximally spaced from a distal segment of the elongate tubular housing and a second configuration in which the distal tip of the second mandril is axially aligned with the distal segment.

In another aspect, a method of performing a percutaneous vascular procedure using a multi-functional wire guide assembly includes steps of moving the multi-functional wire guide assembly into a first configuration to provide a first tip load, and advancing the multi-functional wire guide assembly through a vessel of a patient at the first tip load. The multi-functional wire guide assembly is moved into a second configuration to provide a second tip load that is different than the first tip load and further advanced through the vessel of the patient at the second tip load. The method also includes moving a fluid through an open distal end of an elongate tubular housing of the multi-functional wire guide assembly. The moving steps of the method include moving the second mandril relative to the first mandril.

DETAILED DESCRIPTION

Figure 1:
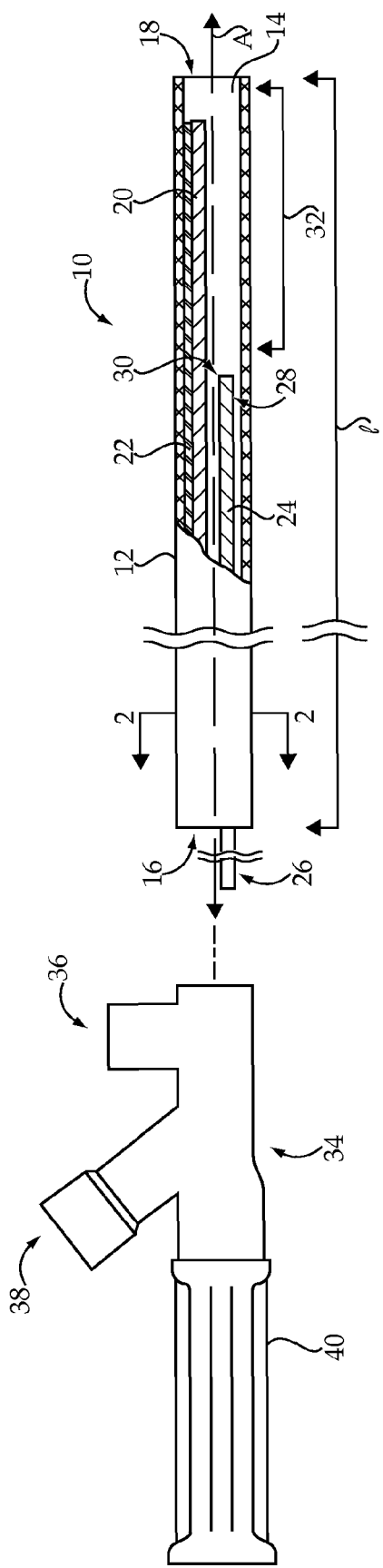
FIG. 1 is a partially sectioned side diagrammatic view of a multi-functional wire guide assembly, according to one embodiment of the present disclosure.

Referring to FIG. 1, there is shown a multi-functional wire guide assembly 10 according to one embodiment of the present disclosure. The multi-functional wire guide assembly 10 includes an elongate tubular housing 12 having a length l and defining a lumen 14 extending from an open proximal end 16 to an open distal end 18 of the elongate tubular housing 12. The elongate tubular housing 12, which may be transparent, may be made from any common medical tube material, such as, for example, a plastic, rubber, silicone, or Teflon® material, and may exhibit both stiffness, or firmness, and flexibility. Materials as well as dimensions may vary depending on the particular application. However, according to one embodiment, the elongate tubular housing 12 may have an outer diameter ranging from about 0.014 inch (in) to about 0.035 in. Further, the elongate tubular housing 12 may be about 60 centimeters (cm) to about 190 cm in length. According to most embodiments, the elongate tubular housing 12 may have a length to diameter ratio of at least about 50 to 1.

The elongate tubular housing 12 may be made from or may include a reinforcement, such as a metal braid or coil, to provide kink resistance and torqueability, while retaining flexibility of the overall housing 12. For embodiments incorporating such reinforcement, the elongate tubular housing 12 may be referred to as a braided sheath. It should be appreciated that the reinforcement may extend the entire axial length l of the elongate tubular housing 12, relative to axis A, or may only be provided on portions of the housing 12. In addition, the elongate tubular housing 12 may include a taper (not shown), such as a proximal to distal taper terminating in the open distal end 18, to provide an atraumatic tip. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The multi-functional wire guide assembly 10 also includes a first mandril 20, also referenced herein as a stationary mandril, positioned within the lumen 14. The stationary mandril 20 may extend a majority of the length l of the elongate tubular housing 12 and may have a fixed position relative to the housing 12. The stationary mandril 20 may be fixed relative to the elongate tubular housing 12 using any of a number of known manufacturing and/or attachment means. For example, a portion of the outer surface of the stationary mandril 20 may be attached to a portion of the inner surface of the elongate tubular housing 12 at an attachment joint 22. The attachment joint 22 may be formed, for example, using adhesion, force convection heating, radio frequency heating, ultrasonic welding, laser bonding, or any other known attachment means.

A second mandril 24, referred to herein as a movable mandril, is also positioned within the lumen 14. The movable mandril 24 may have a length that is greater than the length l of the elongate tubular housing 12 and may be axially movable relative to the housing 12. Specifically, the movable mandril 24 may have a proximal end 26 that is proximally disposed outside the lumen 14 such that it may be manipulated by a clinician. For example, a clinician may, by grasping the proximal end 26, move the movable mandril 24 in the distal and proximal directions to reposition a distal end 28 of the movable mandril 24 relative to the elongate tubular housing 12 and stationary mandril 20. The movable mandril 24 may be completely removed from the lumen 14 of the elongate tubular housing 12 and may have an infinite range of positions from a position at which the distal end 28 of the movable mandril 24 is positioned within the lumen 14 to a position at which the distal end 28 is advanced through the open distal end 18. The distal end 28 may be advanced outside the elongate tubular housing 12 a distance substantially corresponding to the length of the movable mandril 24 minus the length l of the housing 12. As should be appreciated, the clinician may wish to retain a portion of the proximal end 26 of the movable mandril 24 outside the elongate tubular housing 12 that is sufficient to grasp and manipulate the movable mandril 24.

The multi-functional wire guide assembly 10, which may include additional components, as discussed below, may have a first configuration in which a distal tip 30 of the movable mandril 24 is proximally spaced from a distal segment 32 of the elongate tubular housing 12. In a second configuration, which will be shown and discussed below with reference to FIG. 5, the distal tip 30 of the movable mandril 24 is axially aligned with the distal segment 32. In addition to a number of other configurations, the multi-functional wire guide assembly 10 may also have a third configuration in which the distal tip 30 of the movable mandril 24 is distally spaced from the distal segment 32 and outside the lumen 14. The third configuration is shown and discussed in greater detail below with reference to FIG. 6.

Preferably, the stationary mandril 20 is less stiff than the movable mandril 24, and, according to some embodiments, may include nitinol, which is a nickel and titanium alloy known for its superelasticity. Although the stationary mandril 20 may be made from any of a number of materials, it may be desirable to select materials for the stationary mandril 20 that provide a desired level of stability and pushability. Materials for the movable mandril 24 may be selected to provide a desired stiffness. For example, the movable mandril 24 may be used to modify the stiffness of the multi-functional wire guide assembly 10, particularly at or near the distal segment 32, and, thus, materials may be selected to provide a desired change in stiffness. According to one embodiment, the movable mandril 24 may be made from stainless steel.

The multi-functional wire guide assembly 10 may also include a connector 34, or connector assembly, attached at the open proximal end 16 of the elongate tubular housing 12. The connector 34 may be attached to the elongate tubular housing 12 using an interference fit, or using any other known attachment means, and may include one or more ports. For example, the connector 34 may include an injection port 36 that is attached at the open proximal end 16 and fluidly connected to the open distal end 18 for injecting fluids into a vessel or duct of a patient. As should be appreciated, the injection port 36 may include a luer lock to which a syringe may be secured. The connector 34 may also include a wire guide port 38 through which the movable mandril 24 be advanced and withdrawn. Specifically, the movable mandril 24 may be passed through the wire guide port 38 of the connector 34 and through the lumen 14 of the elongate tubular housing 12. Thus, any of the one or more ports of the connector 34 may be in fluid communication with the lumen 14 of the elongate tubular housing 12.

If desired, a handle 40, or gripper, may be provided as part of the connector 34 or may be attached at a proximal end of the connector 34 for improved grasping and manipulation of the multi-functional wire guide assembly 10 by a clinician. Although only a few exemplary components are shown, it should be appreciated that the multi-functional wire guide assembly 10 may include additional known components to change or enhance functionality of the wire guide assembly 10 as desired. Further, it may be desirable to produce multi-functional wire guide assemblies having different configurations depending on particular applications. An exemplary use of one embodiment of the multi-functional wire guide assembly 10 is provided below.

Figure 2:
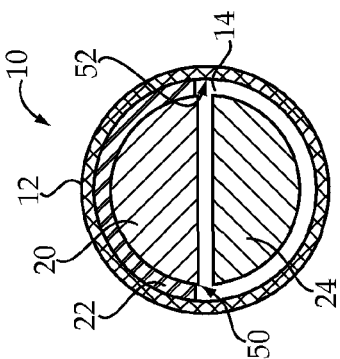
FIG. 2 is a cross sectional view of the multi-functional wire guide assembly of FIG. 1 taken along lines 2-2 according to one aspect of the present disclosure.

Turning now to FIG. 2, a cross-sectional view of the multi-functional wire guide assembly 10, taken along lines 2-2 of FIG. 1, is shown. As shown, each of the stationary mandril 20 and the movable mandril 24 may have a semi-circular cross section, or other cross section selected to maximize sizes of the mandrils 20 and 24 within the lumen 14. However, the mandrils 20 and 24 may have alternative cross sections, which may be selected to provide desired performance of each of the mandrils 20 and 24 and the multi-functional wire guide assembly 10 as a whole. The attachment joint 22 may connect an outer surface 50 of the stationary mandril 20 with an inner surface 52 of the elongate tubular housing 12. According to some embodiments, the attachment joint 22 may be larger or smaller, as desired, and may be continuous or discontinuous both axially and circumferentially.

Figure 3:
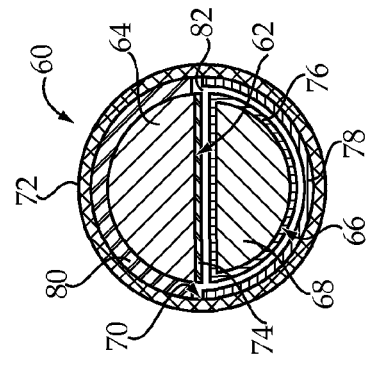
FIG. 3 is a cross sectional view of an alternative embodiment of a multi-functional wire guide assembly, according to another aspect of the present disclosure.

A cross-sectional view of an alternative multi-functional wire guide assembly 60 is shown in FIG. 3. Specifically, according to some embodiments, it may be desirable for at least one of an outer surface 62 of a first, or stationary, mandril 64, an outer surface 66 of a second, or movable, mandril 68, and an inner surface 70 of an elongate tubular housing 72 to include a lubricious coating. As shown in FIG. 3, a portion of the outer surface 62 of the stationary mandril 64 includes a lubricious coating 74, the entire outer surface 66 of the movable mandril 68 includes a lubricious coating 76, and a portion of the inner surface 70 of the elongate tubular housing 72 includes a lubricious coating 78. The embodiment of FIG. 3 also depicts an attachment joint 80 for maintaining a stationary position of the stationary mandril 64 relative to the elongate tubular housing 72. As shown in the embodiment of FIG. 3, and in the previous embodiment, sufficient space within a lumen 82 of the elongate tubular housing 72 may exist to allow the passage of fluid through the lumen 82, even when the movable mandril 68 is occupying the lumen 82.

INDUSTRIAL APPLICABILITY

The present disclosure is generally applicable to medical devices for use in percutaneous vascular procedures, or other procedures involving cavities, ducts, or canals of a patient. More specifically, the present disclosure finds application in procedures that require a plurality of wire guides having different property requirements. Alternatively, or additionally, the present disclosure finds application in procedures that require a wire guide having a changing stiffness measurement, particularly at a distal end thereof. Further, the present disclosure finds application in procedures requiring the use of a catheter, alone or in combination with a wire guide, to perform functions such as, for example, crossing lesions and injecting fluids.

Figure 4:
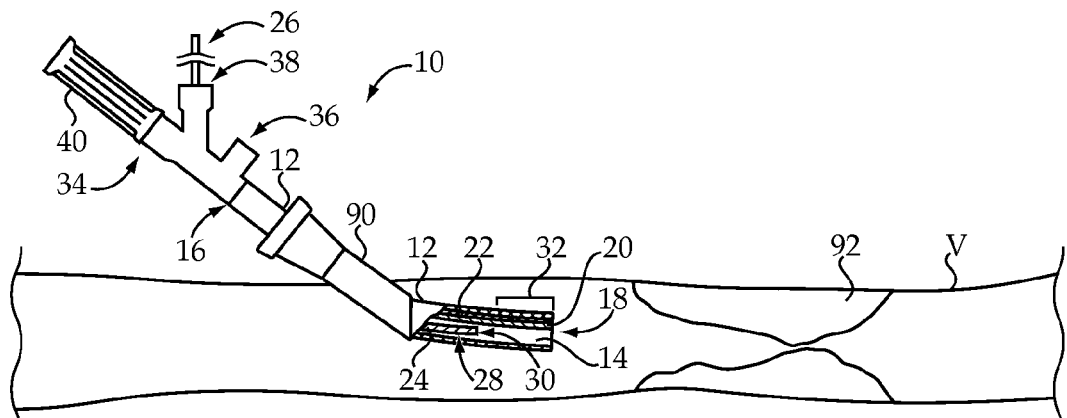
FIG. 4 is a side diagrammatic view of a vascular structure of a patient at one stage of a percutaneous vascular procedure, with the multi-functional wire guide assembly of FIG. 1 shown in a first configuration, according to another aspect of the present disclosure.
Figure 5:
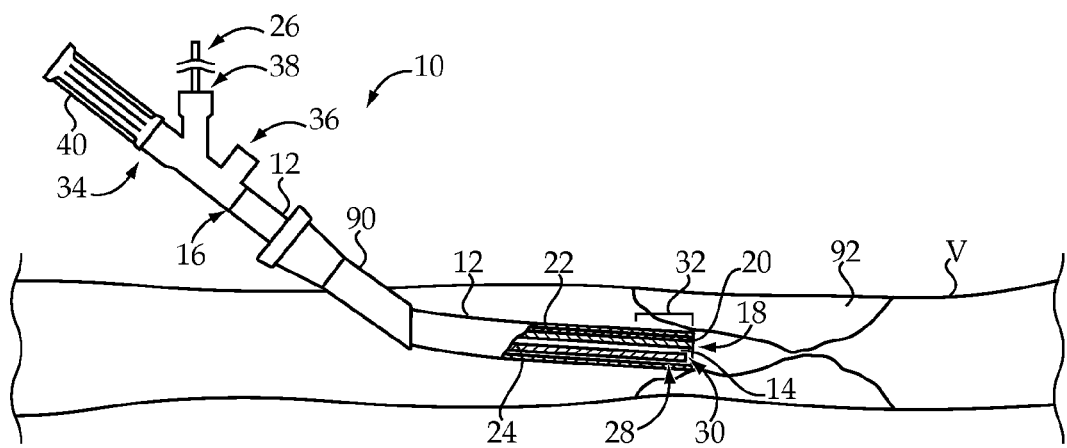
FIG. 5 is a side diagrammatic view of the vascular structure of a patient at another stage of a percutaneous vascular procedure, with the multi-functional wire guide assembly of FIG. 1 shown in a second configuration, according to another aspect of the present disclosure.
Figure 6:
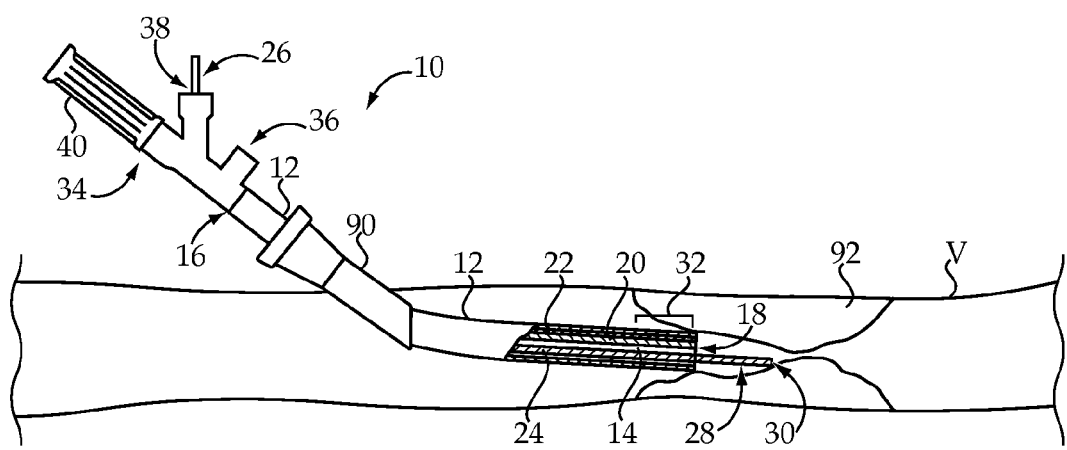
FIG. 6 is a side diagrammatic view of the vascular structure of a patient at yet another stage of a percutaneous vascular procedure, with the multi-functional wire guide assembly of FIG. 1 shown in a third configuration, according to another aspect of the present disclosure.

Referring to FIGS. 4-6, a percutaneous vascular procedure using the multi-functional wire guide assembly 10 of FIG. 1 will be described with reference to a vascular structure V of a patient. As shown in FIG. 4, there is shown a vascular structure V of a patient having a needle, or introducer, 90 positioned therein, at a first stage of a vascular procedure according to one embodiment. At the first stage of the procedure, a clinician may insert the multi-functional wire guide assembly 10 through a tube of the introducer 90 and into the vascular structure V. As shown, the multi-functional wire guide assembly 10 may be initially introduced into the vascular structure V in the first configuration, as shown in FIG. 1, or in any other configuration, selected to provide a desired first tip load. The tip load, as used herein, may refer to a stiffness measurement at the distal segment 32 of the elongate tubular housing 12. It should be appreciated that moving the multi-functional wire guide assembly 10 into the first configuration, or any other configuration, includes moving the movable mandril 24 relative to the stationary mandril 20. The first configuration may provide a decreased stiffness of the multi-functional wire guide assembly 10 at the distal segment 32, since, as should be appreciated, the movable mandril 24 is proximally refracted such that the distal tip 30 of the movable mandril 24 is proximally spaced from the distal segment 32.

A next stage of the percutaneous vascular procedure is shown in FIG. 5. Specifically, FIG. 5 depicts the multi-functional wire guide assembly 10 in a second configuration. The clinician may move the multi-functional wire guide assembly 10 into the second configuration by moving the movable mandril 24 relative to the stationary mandril 20 to provide a second tip load that is different than the first tip load. Specifically, according to the exemplary procedure, the clinician may increase the tip load, or stiffness, at the distal segment 32 by distally advancing the movable mandril 24 such that the distal tip 30 of the movable mandril 24 is axially aligned with the distal segment 32. The multi-functional wire guide assembly 10 may then be further advanced through the patient vessel V at the second tip load. As show, an increased tip load may be required to cross a lesion, or occlusion, 92.

A further stage of the percutaneous vascular procedure is shown in FIG. 6. This stage may include advancing the multi-functional wire guide assembly 10 further through the lesion 92. Crossing the lesion 92 may be facilitated, at least in part, by advancing the distal tip 30 of the movable mandril 24 through the open distal end 18 of the elongate tubular housing 12 and into contact with the lesion 92. Thus, the movable mandril 24 may be used in combination with the elongate tubular housing 12 to break up and cross the lesion 92. In this respect, the elongate tubular housing 12 may function as a catheter that, according to conventional designs, may be used in combination with a wire guide to cross a lesion or occlusion.

Friction occurring during the movement of the multi-functional wire guide assembly 10 into various configurations, such as those described above, may be reduced with a lubricious coating, such as one or more of coatings 74, 76, and 78 shown in FIG. 3, provided on at least one of an outer surface 62 of the stationary mandril 64, an outer surface 66 of the movable mandril 68, and an inner surface 70 of the elongate tubular housing 72. It should be appreciated that the coatings 74, 76, and 78 may be provided only on portions of component surfaces, as desired. The multi-functional wire guide assembly 10 may also include other known enhancements that may improve the functionality of the wire guide assembly 10.

Any of the stages of the procedures described above, or any additional stages, may include moving a fluid through the open distal end 18 of the elongate tubular housing 12. Specifically, for example, any procedure stage may include injecting a fluid into the vessel V of the patient through the injection port 36 attached at the open proximal end 16 of the elongate tubular housing 12, through the lumen 14, and through the open distal end 18. This fluid communication through the elongate tubular housing 12 may facilitate the injection of liquids into the vessel V of the patient at any stage during the advancement of the multi-functional wire guide assembly 10.

The multi-functional wire guide assembly disclosed herein is a single assembly capable of performing a variety of functions that have conventionally been performed using multiple medical devices. Specifically, the wire guide assembly of the present disclosure includes a number of configurations that provide different properties or characteristics that are necessary during different stages of a procedure. Thus, the multi-functional wire guide disclosed herein may reduce the number of devices, such as wire guides and catheters, needed during a medical procedure and, thus, may reduce duration, complexity, and costs associated with the procedure. Further, the reduction in components removed and inserted into the vasculature of a patient may reduce the risk of infection associated with the use of multiple devices. The present wire guide assembly provides this cross-functionality while maintaining overall simplicity, reliability, and manufacturability.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A multi-functional wire guide assembly, comprising:
an elongate tubular housing having a length and defining a lumen extending from an open proximal end of the elongate tubular housing to an open distal end of the elongate tubular housing;
a first mandril positioned within the lumen, extending a majority of the length of the elongate tubular housing, having a portion of an outer surface attached to an inner surface of the elongate tubular housing at an attachment joint, and having a fixed position relative to the elongate tubular housing, and a segment of the attachment joint being remote from a distal end of the first mandril and being remote from the distal end of the elongate tubular housing; and
a second mandril positioned within the lumen, having a length greater than the length of the elongate tubular housing, and axially movable relative to the elongate tubular housing;
wherein the multi-functional wire guide assembly has a first configuration in which a distal tip of the second mandril is proximally spaced from a distal segment of the elongate tubular housing and a second configuration in which the distal tip of the second mandril is axially aligned with the distal segment; and
wherein the first mandril and the second mandril are exposed to fluid passing through the lumen.

2. The multi-functional wire guide assembly of claim 1, wherein the first mandril is less stiff than the second mandril.

3. The multi-functional wire guide assembly of claim 2, wherein the first mandril includes nitinol.

4. The multi-functional wire guide assembly of claim 2, wherein the second mandril includes stainless steel.

5. The multi-functional wire guide assembly of claim 2, wherein at least one of an outer surface of the first mandril, an outer surface of the second mandril, and an inner surface of the elongate tubular housing includes a lubricious coating.

6. The multi-functional wire guide assembly of claim 5, wherein the elongate tubular housing includes a braided sheath.

7. The multi-functional wire guide assembly of claim 5, wherein each of the first mandril and the second mandril has a semi-circular cross section.

8. The multi-functional wire guide assembly of claim 5, further including an injection port attached at the open proximal end of the elongate tubular housing, wherein the injection port is fluidly connected to the open distal end.

9. The multi-functional wire guide assembly of claim 1, wherein the multi-functional wire guide assembly has a third configuration in which the distal tip of the second mandril is distally spaced from the distal segment and outside the lumen.

10. A method of performing a percutaneous vascular procedure using a multi-functional wire guide assembly, wherein the multi-functional wire guide assembly includes an elongate tubular housing having a length and defining a lumen extending from an open proximal end of the elongate tubular housing to an open distal end of the elongate tubular housing, a first mandril positioned within the lumen, extending a majority of the length of the elongate tubular housing, having a portion of an outer surface attached to an inner surface of the elongate tubular housing at an attachment joint, and having a fixed position relative to the elongate tubular housing, and a segment of the attachment joint being remote from a distal end of the first mandril and being remote from the distal end of the elongate tubular housing, and a second mandril positioned within the lumen, having a length greater than the length of the elongate tubular housing, and axially movable relative to the elongate tubular housing, the method comprising steps of:
moving the multi-functional wire guide assembly into a first configuration to provide a first tip load;
advancing the multi-functional wire guide assembly through a vessel of a patient at the first tip load;
moving the multi-functional wire guide assembly into a second configuration to provide a second tip load that is different than the first tip load;
further advancing the multi-functional wire guide assembly through the vessel of the patient at the second tip load; and
moving a fluid through the open distal end of the elongate tubular housing;
exposing the first mandril and the second mandril to the fluid moving through the lumen of the elongate tubular member;
wherein the steps of moving the multi-functional wire guide assembly include moving the second mandril relative to the first mandril, which has the portion of the outer surface between opposite ends attached to the inner surface of the elongate tubular housing.

11. The method of claim 10, wherein the first moving step includes decreasing a stiffness of the multi-functional wire guide assembly at a distal segment of the elongate tubular housing by proximally retracting the second mandril such that a distal tip of the second mandril is proximally spaced from the distal segment.

12. The method of claim 11, wherein the second moving step includes increasing the stiffness at the distal segment by distally advancing the second mandril such that the distal tip of the second mandril is axially aligned with the distal segment.

13. The method of claim 10, further including reducing friction during the steps of moving the multi-functional wire guide assembly with a lubricious coating on at least one of an outer surface of the first mandril, an outer surface of the second mandril, and an inner surface of the elongate tubular.

14. The method of claim 10, further including: advancing the multi-functional wire guide assembly toward a lesion; and crossing the lesion, at least in part, by advancing a distal tip of the second mandril through the open distal end of the elongate tubular housing and into contact with the lesion.

15. The method of claim 10, wherein the step of moving a fluid includes injecting a liquid into the vessel of the patient through an injection port attached at the open proximal end of the elongate tubular housing, through the lumen, and through the open distal end.

* * * * *